United States Patent
Fletcher et al.

(10) Patent No.: US 6,261,543 B1
(45) Date of Patent: Jul. 17, 2001

(54) ANTIPERSPIRANT COMPOSITIONS

(75) Inventors: Neil Robert Fletcher, Wirral (GB); Miyuki Kanda, Tochigi-ken (JP); Howard Allen Ketelson, London (CA); Graham Andrew Turner, Wirral (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/416,104

(22) Filed: Oct. 12, 1999

(30) Foreign Application Priority Data

Oct. 15, 1998 (GB) .................................................. 9822518

(51) Int. Cl.[7] ............................... A61K 7/32; A61K 7/34; A61K 7/38; A61K 7/00; A61K 31/74
(52) U.S. Cl. ................................ 424/65; 424/66; 424/68; 424/400; 424/401; 424/78.02; 424/78.08
(58) Field of Search ................................ 424/65, 66, 68, 424/400, 401, 78.02, 78.08

(56) References Cited

U.S. PATENT DOCUMENTS 4,803,195  2/1989  Holzner ..................................... 512/4

FOREIGN PATENT DOCUMENTS

| 0676192 | 10/1995 | (EP) . |
| 91/15947 | 10/1991 | (WO) . |
| 96/23483 | 8/1996 | (WO) . |

OTHER PUBLICATIONS

International Search Report Application No. PCT/EP 99/07428 mailed Mar. 17, 2000.

Primary Examiner—Shelley A. Dodson
(74) Attorney, Agent, or Firm—Matthew Boxer

(57) ABSTRACT

Antiperspirant emulsions which exhibit excellent phase stability even in the presence of an effective concentration of antiperspirant salts in solution and which are thickened are obtainable by dispersing a hydratable polymer and particularly an amphoteric or cationic modified starch in an aqueous emulsion forming a viscous emulsion, often at an elevated temperature, subjecting the emulsion to high shear, thereby reducing the droplet size of the dispersed oil phase, bringing the emulsion to below 40° C. and introducing the antiperspirant, preferably in aqueous solution. The viscous emulsion subjected to high shear mixing desirably has a Sheer Stress of 10 to 500 Pa. The resultant emulsions show good phase stability even when they contain aluminium/zirconium antiperspirant salts that promote instability and even at elevated storage temperatures such as at 50° C.

50 Claims, No Drawings

ANTIPERSPIRANT COMPOSITIONS

The present invention relates to compositions containing an antiperspirant, particularly to emulsion compositions and to a process for their production.

1. Technical Field

A variety of applicators have been described and/or commercialised for topically applying antiperspirant compositions to human skin. Amongst applicators which have found favour over the years, there can be listed roll-ons, pump or squeeze sprays, and pressurised aerosols which normally or often employ flowable liquids and creams or sticks which are sometimes produced from flowable liquids.

Antiperspirant formulations have been proposed or commercialised in a number of different physical forms, including powders, suspension or emulsions structured solids or creams and solution or emulsion liquids. The present invention is particularly directed to emulsions in liquid form or optionally after structuring and especially to oil in water emulsions.

2. Background and Prior Art

Emulsions can be made by mixing an aqueous phase with an oil phase in the presence of an emulsifier or blend of emulsifiers, optionally at an elevated temperature selected to dissolve desired ingredients in one or other of the phases. An established method to produce fine droplet dispersion emulsions is the so-called phase inversion temperature or PIT process, the emulsifier, aqueous phase and the oil phase are mixed at, or the mixture heated to, a temperature at which phase inversion occurs, and thereafter the emulsion is permitted to cool or is cooled to ambient.

Emulsions represent a potentially convenient form for antiperspirant compositions in that it is theoretically possible to obtain fine dispersions of the one phase in the other. This can result, if sufficiently fine, in the formation of transparent or nearly transparent formulations which a number of consumers perceive to be beneficial.

However, stability problems can arise for emulsions. Emulsions (not microemulsions) are thermodynamically unstable and accordingly rely for their apparent stability on de-emulsification being kinetically hindered. De-emulsification can be exacerbated by storage of the formulations at high ambient temperatures, such as can arise in warehouses during summer months, especially in tropical or central continental or Mediterranean climates, or by a temperature cycle in which the formulations are subjected to cyclical heating and cooling. Additionally, the presence of elevated concentrations of salts in the aqueous phase encourages de-emulsification. This is of direct pertinence to antiperspirant emulsions, and especially aluminium or aluminium/zirconium emulsions which incorporate a substantial concentration of antiperspirant active salts in the aqueous phase. Accordingly, teaching concerning the stability of emulsions which do not contain a significant concentration of antiperspirant salts cannot be transferred unquestioningly to antiperspirant-containing emulsions.

A number of publications have described the preparation of water in oil emulsions, or anhydrous emulsions, such as GB-A-2113706 to Colgate-Palmolive Co, GB-A-2009617 to Petersen/Puritan, Inc and GB-A-20968891 to Colgate-Palmolive Co. These, however, do not provide suitable teaching for stabilising oil in water emulsions.

In DE-A-4337041 to Henkel, there is described a process for producing oil in water emulsions employing a PIT technique, but the disclosure is silent about the incorporation of antiperspirant actives. In practice, the addition of antiperspirant actives in attractive concentrations, e.g. at a concentration which offers substantial sweat reduction to the Henkel compositions impairs their stability.

In WO 96/23483 to Bristol Meyers Squibb, there is described a process producing emulsions at below the phase inversion temperature of the emulsion and employing tightly defined combinations of ingredients. They are in the form of microemulsions.

In U.S. Pat. No. 4,499,069 to Gillette, there is described the preparation of a stable emulsion employing a surfactant mixture containing polyethylene glycol (21) stearyl ether, but this does not provide a transferable teaching on how to achieve stability, because the document discloses that closely related surfactants such as polyethylene glycol (20) stearyl ether and other polyglycol ether mixtures did not produce stable emulsions. Moreover, it employs a hydrophobic polymer.

Aqueous emulsions can also suffer from an impaired sensory perception by users, and particularly emulsions containing particularly efficacious antiperspirant salts.

Accordingly, there is a continuing need for a method that is capable of producing stable emulsions containing an antiperspirant active salt. Additionally or alternatively, there remains an outstanding desire for aqueous emulsions which are both sensorially pleasing and effective in reduction of perspirancy. Alternatively or additionally, there remains a need for a method or an alternative method to produce an emulsion comprising a fine dispersion and containing an antiperspirant active salt, and particularly a process to produce an emulsion which is stable. Furthermore, there remains a need for a process which can produce not only a stable antiperspirant emulsion offering acceptable sweat reduction, but one that exhibits sensorially pleasing characteristics.

OBJECTS OF THE INVENTION

It is an object of at least one aspect of the present invention to provide a process that is capable producing an antiperspirant emulsion having a small mean droplet size.

It is an object of at least some embodiments of the present invention to provide an antiperspirant emulsion which is resistant to phase separation, and particularly in preferred embodiments offering resistance to phase separation during storage at above standard temperature.

It is an additional or alternative object of certain or other embodiments of the present invention to provide aqueous emulsions containing a high concentration of a salt or salts which is resistant to phase separation and particularly in preferred embodiments offering resistance to phase separation during storage at above standard temperature.

SUMMARY OF THE INVENTION

According to one aspect of the present invention, there is provided a process for producing an antiperspirant—containing emulsion comprising the steps of:

i) dispersing a hydratable polymer in an aqueous emulsion comprising an aqueous phase, an oil phase and an emulsifier at a concentration and at a temperature selected such that the polymer is hydrated and the viscosity of the emulsion is substantially higher than in the absence of the polymer, ii) subjecting the emulsion containing the dispersion of hydratable polymer to high shear, iii) agitating the emulsion until its temperature has attained a temperature below 40° C. and iv) introducing an antiperspirant salt into the emulsion with agitation to form an antiperspirant emulsion.

A hydratable polymer is one which exhibits swelling when brought into contact with an aqueous medium. There is a tendency for the polymer chains to uncoil during hydration and thereby expand. This is in contrast with hydrophobic polymers which do not exhibit swelling.

By subjecting a viscous emulsion containing a dispersed hydratable polymer to high shear, it is possible to obtain an emulsion in which its dispersed phase has a reduced mean droplet size. The emulsions obtained in the present invention are not micro-emulsions. Without being restricted to any theory as to the mode by which the invention result is achieved, it is believed that the hydratable polymer tends to hydrate at the selected processing temperature subsisting in step i) and produces a thickened aqueous phase. When the hydratable polymer is dispersed through the emulsion and subjected to high shear, the elevated viscosity of the emulsion induces rupturing of the droplets. By contrast, without dispersion of the polymer and in a thin formulation, efficient droplet rupturing has not been observed.

The temperature and concentration of the hydratable polymer to provide a significant increase in the viscosity of the emulsion is related to the choice of hydratable polymer that is employed. The temperature is normally selected in the range of from ambient to 100° C. For some hydratable polymers, such as for example modified starches described subsequently herein, it is highly preferable to employ an elevated temperature such as above 60° C., eg 70 to 95° C. to encourage hydration. For other hydratable polymers a lower temperature can be employed during the polymer hydration step. Some hydratable polymers benefit from a high concentration, whereas for a number of preferred polymers, such as especially for preferred modified starches, it is possible to attain an acceptable increase in viscosity at comparatively low concentrations.

The emulsions contemplated herein without the hydratable polymer, would often, though not essentially, have a viscosity in the range of 25 to 200 mPa.s. The hydratable polymer when incorporated effectively can result in the emulsion that is in the region of orders of magnitude higher than the range of polymer-free emulsion, and advantageously at least 5000 mPa.s. In practice, it can be often convenient to conduct ranging trials to determine the concentration of polymer and temperature that is acceptable for advantageous polymer dispersion and hydration.

The emulsion containing the hydratable polymer which is advantageously subjected to high shear mixing conveniently has a Newtonian plateau viscosity at a shear stress of 10 Pa of from 50 000 to $2 \times 10^7$ mPa.s, and particularly up to $1 \times 10^7$ mPa.s. Herein, unless otherwise explicitly stated, viscosity data refers to measurements conducted at ambient temperature (22° C.), using a Brookfield DV-1 viscometer RV spindle at 10 rpm. Where the emulsion would have a higher temperature in normal operation, the viscosity measurement is conducted after the emulsion has cooled.

Very desirably, the emulsion for high shear mixing in step 2 has a Critical Stress of from 1 to 5000 Pa, especially at least 5 Pa, and most especially at least 10 Pa, particularly not more than 2000 Pa and most particularly not more than 500 Pa. The Critical Stress of an emulsion is the stress at which the viscosity of the emulsion is half its Newtonian plateau viscosity. It is particularly desirable to generate an emulsion in step 1 which simultaneously satisfies the above identified ranges for low shear stress Newtonian plateau viscosity, particularly 50 to 10 000 mPa.s, and the ranges for Critical Stress, particularly 10 to 500 Pa.

The process of the present invention can advantageously reduce the droplets in the oil phase of the emulsion to below a mean droplet size of 1 µm. Despite this reduction in droplet size, the resultant product is not a micro-emulsion.

The emulsion produced by the invention process can retain the dispersed phase in small droplet size when it is subsequently diluted with a salt, such as an antiperspirant salt at a topically effective concentration, which is often introduced as a concentrated aqueous solution.

In a second aspect of the present invention, there is provided an antiperspirant emulsion which comprises an aqueous phase containing an antiperspirant salt, an oil phase and an emulsifier characterised in that the aqueous phase contains a dispersed hydratable polymer at a concentration which is effective to increase substantially the viscosity of the emulsion prior to introduction of the antiperspirant salt and which permits a reduction in size of the droplets in the oil phase and an antiperspirant salt at a topically effective concentration and the dispersed oil phase has a mean droplet size of below 1 µm.

In the invention compositions according to the second aspect, the concentration of hydratable polymer is chosen in accordance with its capability to be hydrated and to generate the desired viscosity of the emulsion. The concentration of polymer is normally chosen in the range of at least 0.25% w/w hydratable polymer and for preferred polymers, desirably from up to 5% polymer. For less hydratable polymers, higher concentrations can be contemplated.

Advantageously, such a composition containing dispersed droplets of mean size below 1 µm, in the form of an oil in water emulsion demonstrates resistance against phase separation, even when it contains a high concentration of antiperspirant salts and even when it is stored at a temperature above standard temperature. The concentration of antiperspirant salts considered to be topically effective varies at least in part according to prevailing national regulations, but is normally at least 5% w/w antiperspirant salts, and frequently at least 10% salts.

Compositions according to the second aspect of the present invention have demonstrated improved sensory properties, and especially improved smoothness, and at least some of the invention emulsions have a capability to provide one or more desirable properties of improved smoothness on application, reduced stickiness, reduced greasy feel or reduced visibility of deposits during or shortly after topical application, for example in measurements made 1 hour after application.

In a third aspect of the present invention, there is provided an antiperspirant composition comprising an aqueous emulsion containing an effective concentration of an antiperspirant salt which is stable to phase separation. By stable to phase separation is meant that the emulsion is free from creaming after storage for 14 days at 50° C.

Such a composition, which would usually comprise an oil phase dispersed in an aqueous phase, can be obtained by employing a process according to the first aspect of the present invention. Advantageously, the stable emulsion comprises an oil phase in small droplets obtainable by subjecting a dispersion of an oil phase in an aqueous phase to shear mixing in the presence of an hydratable polymer, especially an hydratable starch. In many desired emulsions satisfying the third aspect of the present invention, the emulsion is thickened, for example having a viscosity of from 500 mPa.s, particularly over 1000 mPa.s and in many instances less than 10000 mPa.s. Such emulsions demonstrate the benefit of stability whilst remaining thin enough to be employed as a roll-on, a noteworthy achievement, though they can also retain their stability if they are thickened to a higher viscosity.

In preferred embodiments of the invention, the stable emulsions of the third aspect demonstrate one or more improved sensory properties, such as in particular improved smoothness on application, and/or one or more of stickiness or greasiness on application or visibility of deposits shortly after application. Such improved properties can be apparent especially when the emulsion contains a zirconium salt as active antiperspirant.

In a further aspect of the present invention there is provided an emulsion which comprises an aqueous phase containing a salt, an oil phase and an emulsifier characterised in that the aqueous phase contains a dispersed hydratable polymer at a concentration which is effective to increase substantially the viscosity of the emulsion prior to introduction of the salt and which permits a reduction in size of the droplets in the oil phase and at least a topically effective concentration of dissolved salt and the dispersed oil phase has a mean droplet size of below 1 $\mu$m.

Preferably, the aqueous phase is acidic.

DETAILED DESCRIPTION OF THE INVENTION

The process of the present invention comprises as a first step dispersing an hydratable polymer in an emulsion at a temperature chosen in conjunction with the hydration characteristics of the polymer. The temperature range within which the temperature is selected to conduct the process is usually from ambient to 100° C. For some polymers, the dispersion can be carried out at ambient or slightly higher, such as from about 20 to about 40° C. For others a higher temperature is advantageous, such as especially at least 60° C. and particularly at a temperature selected in the range of 70° C. to 95° C. The polymer typically is dispersed within the aqueous phase.

In one method of operation, it is highly desirable to produce the emulsion prior to the introduction of the hydratable polymer. The emulsion can be prepared conveniently by producing separately an aqueous phase and an oil phase, at least one of the phases containing an emulsifier, heating them, if necessary, to an elevated temperature. In some convenient embodiments, the temperature at which the emulsion is formed is a temperature which is the same as or maybe a little higher than the temperature at which the first step is conducted, and then mixing the two phases. In another method of operation, and particularly a method operated at elevated temperature, the emulsion is not completely formed prior to addition of the polymer, but the polymer is added as the emulsion is forming, causing a simultaneous increase in viscosity of the emulsion during its formation.

Desirably, the hydratable polymer is dispersed into the preformed emulsion or emulsion as it is forming, commonly being introduced as a powder or flaky solid. The polymer can, if desired, be at least partially pre-hydrated with water prior to its addition to the emulsion or constituents forming the emulsion. Alternatively, the polymer can be added in the form of a slurry, i.e. suspended or dispersed in the oil phase or a component thereof. This alternative may allow more uniform distribution of the polymer in the emulsion before hydration commences and may encourage subsequent hydration to be more efficient.

In a number of suitable embodiments, the emulsion in step i) comprises from 25 to 75 parts by weight aqueous phase, 2 to 20 parts by weight oil phase and 1 to 7.5 parts by weight emulsifier, the weight ratio of water to oil phases preferably being in the range 2.5:1 to 30:1. In many instances, the weight ratio of emulsifier to oil phase in step i) is chosen in the range of from 2:1 to 1:7 and in certain particularly liked processes from 3:2 to 5:1. It is desirable, in at least some embodiments, for the weight ratio of hydratable polymer to oil phase to be chosen in the range of from 1:2 to 1:20, preferably 1:2.5 to 1:12.

In the second step of the present invention process, the emulsion containing dispersed hydratable polymer is subjected to shear. The shear step is most conveniently conducted at the same or a similar temperature to that of step i). By so doing, the droplet size of the dispersed oil phase is reduced. Preferably, the shear rate and duration of the period when the emulsion is selected to shear are so selected in conjunction with the choice of hydratable polymer, its concentration and the viscosity of the emulsion that the droplet size of the dispersed oil phase is reduced to a mean of below 1 $\mu$m. By suitably selecting and controlling the aforementioned variables, it is possible to obtain emulsions in which the mean droplet size of the oil phase is in the range of from 0.3 to 0.7 $\mu$m.

The shear process step 2 is desirably conducted under high shear conditions. For example this can comprise mixing the formulation using a high speed mixer, operating at a rate of at least 200 rpm, particularly 2000 to 10000 rpm and particularly from 3000 to 5000 rpm.

Advantageously, by conducting a process as described herein for reducing the droplet size of the oil phase, it is possible to obtain a resultant distribution of sizes of droplets which is narrow, such as 90% within a range of from half to twice the mean droplet size. In practice this means that emulsions can be obtained which contain only a relatively small proportion of larger droplets. Droplet size distribution of the emulsion is often controlled during processing to be significantly below 1 $\mu$m such as from 0.3 to 0.8 $\mu$m, with a consequence that the fraction of droplets of diameter above 1 $\mu$m can be small, and even very small.

The dispersion of the hydratable polymer in step i) can in at least some instances be conducted under high shear conditions so that steps i) and ii) can blend into each other. The viscosity of the emulsion manifestly increases during the course of step i). Processing under high shear in step 2 is carried out when the emulsion has attained a relatively high viscosity, or if high shear conditions commence in step 1 when the emulsion has a low viscosity, such conditions continue after a high viscosity has been attained. The viscosity of the composition normally increases from a thin composition, such as one having a viscosity of below about 500 mPa.s, eg in the range of 25 to 200 mPa.s, in many instances to at least the region of 5000 mPa.s. The concentration of hydratable polymer is often chosen in conjunction with operating conditions to permit the formulation to increase in viscosity to within the range of 5000 to 25000 mPa.s, and in a number of convenient processes to within the range of 10000 to 20000 mPa.s during step 1 and/or step 2.

Step 1 is normally continued until the polymer is manifestly dispersed. The processing time in practice for step 1 will depend to at least some extent on the temperature at which the step is conducted and the rate at which the selected polymer is able to be hydrated. The process can be terminated when the emulsion has a suitably enhanced viscosity. Step 1 normally lasts at least 2 minutes, and is usually selected in the range of up to 60 minutes, preferably from 5 to 20 minutes, but under adverse processing conditions, it can last longer, if beneficial.

Step 2 usually lasts at least 2 minutes and is often selected in the range of up to 60 minutes, and preferably from 5 to 20 minutes. Where steps 1 and 2 are conducted under the same temperature and mixing conditions, it is often convenient to contemplate a combined processing time for the two steps of from 10 to 120 minutes, and preferably 20 to 40 minutes.

The proportion of preferred dispersed hydratable polymer in the emulsion is normally chosen within the range of 0.25–5.0% by weight and particularly in the range of from 0.5% to 2% by weight.

The hydratable polymer is desirably selected in terms of material such that an aqueous emulsion containing a dispersion of it after step i) is has a Shear Stress of at least 1 Pa, preferably at least 5 Pa and especially at least 10 Pa, particularly from 10 to 500 Pa.

The polymer material is advantageously an amphoteric or cationic modified starch, such as a modified potato starch. Alternative sources of starch for modification include corn, rice, sago, tapioca waxy maize, sorghum. oats and high amylase corn. The cationic modified starch is normally starch which has been substituted by an onium group, such an N, S or P containing onium group, and especially an N onium such as an ammonium or quarternised imino group. The onium group is typically bonded to the starch substrate via an alkylene ether group, such as particularly a di or polymethylene ether group containing 2 to 10 carbons, eg —O—$(CH_2)_2$—. The onium and particularly the ammonium group in many instances contains at least 2 alkyl substituents and particularly groups containing from 1 to 20 carbons, especially 1 to 4 carbons, such as methyl or ethyl.

Amphoteric starches for employment in the present invention commonly comprise amino or imino substituted starches, and especially amino substituted starches which have been further substituted by an acid substituent, such as phosphate, phosphonate, sulphate, sulphonate or especially carboxylate, or in corresponding acid form. The amine or imine group is typically bonded to the starch substrate via an alkylene ether, such as in the above-mentioned cationic starches, for example —O—$(CH_2)_2$—. It is particularly suitable to employ an amphoteric starch which satisfies the formula:

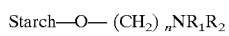
Starch—O—$(CH_2)_n NR_1 R_2$ in which n is from 1 to 4, preferably 2, and $R_1$ and $R_2$ each represents an alkylene carboxylic acid, preferably containing from 2 to 6 and particularly 3 carbons.

In a number of embodiments, it has been found to be especially suitable to employ from 0.5 to 2% w/w of an amphoteric modified starch.

In the third step, where step ii) is conducted at elevated temperature, such as in the range of 70 to 95° C., the emulsion is cooled or allowed to cool to below 40° C., and typically in the range of from 20 to 35° C., encompassing ambient temperature in many factories. Where step ii) is conducted at a lower temperature in the region of ambient or slightly above, it will be recognised that a temperature of below 40° C. is attained without additional action, or possibly by dilution with the antiperspirant or other aqueous salt.

In the fourth step, an antiperspirant, or possibly an alternative or additional salt, is mixed with the cooled emulsion. The fourth step is usually conducted at the temperature obtained by mixing the cooled emulsion with ambient temperature antiperspirant, so that it is often at between 20 and 30° C. By delaying introduction of the salt until the emulsion has cooled, the risk is reduced of the salt destabilising the emulsion. During steps iii) and iv), it is of practical benefit to continue to agitate the emulsion and it is often convenient to employ high shear conditions, such as those employed during step ii). The antiperspirant salt is most conveniently introduced in the form of a concentrated aqueous solution, for example having a weight concentration of between 30 and 55% of the solution. Thereby, in step iv), the water content of the emulsion is also increased.

It is often convenient to conduct all of steps i) to iv) under conditions of high shear.

The introduction of the hydratable polymer into the emulsion, and particularly the modified starch, results in a thickening of the emulsion, not only during the manufacturing process, but also after the introduction of the antiperspirant salt. In practice, it is often desirable to employ sufficient polymer for the emulsion containing the antiperspirant or other salt to attain a viscosity of at least 1000 mPa.s, often and in a number of convenient emulsions in the range of from 1500 to 5000 mPa.s. This can enable the emulsion to be tailored to provide simultaneously phase stability and a suitable viscosity for easy employment in roll-on dispensers. The employment of more viscous formulations, such as in the range of 10000 to 25000 mPa.s by employing, where needed, additional thickener can permit emulsions described herein to be applied using cream dispensers.

The aqueous emulsions produced herein demonstrate resistance to phase separation. In particular, it is possible to produce emulsions by the invention process which are stable to storage at an elevated temperature, and in particular do not cream after storage at a temperature controlled at 50° C. for fourteen days. Such stable formulations also demonstrate resistance to phase separation during temperature cycling, such as in a conventional test in which the formulation is subjected alternately to 12 hour periods at temperatures controlled to 0 and 45° C.

A further way of demonstrating stability of the invention emulsions comprises measuring the droplet size distribution of the emulsion initially and after elapsed periods of storage under controlled temperature conditions, particularly 50° C. Stability is shown by the mean droplet size not varying with storage. Formulations according to the present invention have demonstrated such a stability pattern. By contrast, related formulations with the presence of the hydratable polymer have shown considerable instability in the emulsion within a short storage period, even as short as a day. Instability is typically manifested by the larger droplets coalescing, leaving the smaller droplets in suspension, and thereby resulting in a substantial alteration in the mean droplet size as measured eg by a conventional Malvern particle size analyser, the measurements being conducted on a sample taken from halfway up the height of the stored formulation.

Aqueous Phase

It will be recognised that the incorporation of antiperspirant salts, and particularly zirconium salts, poses a stringent challenge to the phase stability of emulsions. Sufficient salt is preferably introduced so that resultant emulsion contains at least 10% w/w salt, such as 10 to 50% w/w and particularly 20 to 40% salt. A lower concentration of antiperspirant salt can be incorporated, such as from 1 to 10% w/w, and more desirably 5 to 10% w/w, but it will be recognised that at such lower concentrations the salt acts to a greater extent in the capacity of deodorisation. The salt is wholly or predominantly an antiperspirant salt when the emulsion is intended for topical application to the human body to control perspiration, but other topically effective water-soluble salts can be contemplated where the emulsion is intended for other functions.

The antiperspirant salt often comprises aluminium, zirconium, mixed aluminium/zirconium salts, and titanium salts, including both inorganic salts and organic salts and complexes. Preferred astringent salts include aluminium, zirconium and aluminium/zirconium halides and halohydrate salts, such as chlorohydrates.

Astringent aluminium salts include aluminium chloride and aluminium halohydrates having the general formula $Al_2(OH)_xQy.XH_2O$ in which Q represents chlorine, bromine or iodine, x is from 2 to 5 and x+y=6, x and y being either integers or non-integers and X being from 0 to 6.

A range of zirconium salts which can be employed in antiperspirant compositions herein is represented by the following empirical general formula: $ZrO(OH)_{2n-nz}B_z$ in which z is an integer or non-integer in the range of from 0.9 to 2.0, n is the valency of B, 2−nZ is at least 0 and B is selected from the group consisting of halides, including chloride, sulphamate, sulphate and mixtures thereof.

It will be recognised that the above-identified formulae for aluminium and zirconium salts are greatly simplified and encompass compounds having co-ordinated and/or bound water in various quantities as well as polymeric species and mixtures and complexes.

Antiperspirant complexes based on the above-mentioned astringent salts are known and employable in the present invention. By way of example, complexes of aluminium, zirconium and aminoacids such as glycine are disclosed in U.S. Pat. No. 3,792,068 (Luedders et al). Certain of those complexes or complexes with related structures are commonly called ZAG in the literature. One desirable class of complexes which exhibit structure like ZAG comprise aluminium chlorohydrate, including that satisfying the formula $Al(OH)_5Cl.2H_2O$ complexed with aminoacids or other complexing agents. A preferred class of zirconium-based complexes which exhibit structures like ZAG comprise zirconylchlorohydrate of empirical formula $ZrO(OH)_{2-a}Cl_2.nH_2O$ in which a is a non-integer in the range of from 1.5 to 1.87 and n is from 1 to 7 complexed with amino acids or other complexing agents. Activated ZAG complexes can be employed as antiperspirant active in the present invention, such as the materials disclosed in U.S. Pat. No. 5,486,347 (Callaghan et al).

It is particularly desirable to employ herein zirconium-containing antiperspirant salts, such as complexes containing zirconium and aluminium, in that such compounds have demonstrated the greatest antiperspirant efficacy.

Other actives which can be contemplated for employment as appropriate in compositions produced and/or dispensed in accordance with the present invention comprise water-soluble titanium salts such as hydroxycarboxylates, e.g. citrate or lactate.

It is an advantage that by producing oil in water emulsions containing the very small size droplets by the process described herein and particularly using preferred modified starches as hydratable polymer in such a process, it is possible to obtain emulsions which exhibit superior sensory properties, such as smoothness of application (glide) and can exhibit additionally or alternatively a reduced sensation of stickiness and/or greasiness on topical application. Moreover, it is possible to obtain emulsions exhibiting phase stability. By employing the zirconium-containing salts, it is possible to combine the use of the intrinsically most efficacious antiperspirant with emulsion phase stability, even at elevated temperature such as in the region of 50° C., the test temperature, and/or improved sensory perception, including particularly improved glide.

The aqueous phase can additionally incorporate one or more water soluble emollients and/or active constituents. If desired, a water soluble monohydric, dihydric or polyhydric alcohol can be included. Monohydric alcohols include C1 to C4 alcohols such as especially ethanol, or propanol or isopropanol. The proportion of monohydric alcohols is often from 0 to 20% w/w. Dihydric alcohols which can be incorporated include ethylene glycol and propylene glycol, such as in an amount of from 0 to 10% w/w. It will be understood, however, that many highly desirable emulsions according to the present invention are free from either or both monohydric and dihydric alcohols.

It is often advantageous to incorporate a water soluble polyhydric alcohol, such as in an amount of up to 10% w/w and especially from 1 to 5% w/w in the invention compositions. Favoured examples of polyhydric alcohols include sorbitol and glycerol which can moisturise human skin. Glycerol is especially preferred.

The Oil Phase

The oil phase of the oil in water emulsions of the present invention is a proportion of the composition which can be dispersed, and normally constitutes from about 1 to 25% w/w of the emulsions described herein. It comprises one or more hydrophobic materials or materials which are water-immiscible or no better than poorly miscible. Such materials often provide emollient or other beneficial properties, such as fragrance, and/or act as carriers for other emollient/beneficial materials.

The oil phase is often selected from one or more silicone oils, liquid hydrocarbons, and water-insoluble alcohols or aliphatic ethers or aliphatic or aromatic esters. Many of the components of the oil phase are liquid at ambient temperature or melt at up to about 70° C. Other melt below 100° C.

Silicone oils are preferred constituents of the oil phase and such oils employable herein are normally chosen from polysiloxanes and particularly polyalkylsiloxanes, or from silicone glycols. The silicone oils can be either volatile or non-volatile or a mixture of both, but preferably volatile oils constitute the major proportion of silicone oils. The silicone oil often provides carrier functions in addition to contributing to emolliency, and often forms the balance of the oil phase. In some advantageous embodiments, the silicone oils are present in a proportion of from 1 to 15% w/w and particularly from 2 to 10% w/w.

Volatile silicones are often chosen from cyclic polysiloxanes of formula —[—$SiRR'$—]$_n$— in which R and R' represent an alkyl, preferably a methyl group and n is from 3 to 8 and especially 4 or 5, otherwise referred to as cyclomethicones. Other suitable volatile silicones can be selected from low molecular weight linear polysiloxanes of formula $SiRR'R''$—[—$SiRR'$—]$_m$—$SiRR'R''$ in which R R' and R" each represent an alkyl, preferably a methyl group and m is from 1 to 7 and especially 2 or 3. The volatile silicone oils generally have a viscosity of from about 1 to 10 mPa.s at 25° C. Examples of volatile silicones are Dow Corning 225, 244, 245, 344, 345, 1732, 5732, 5750, (all available from the Dow Corning Corp.) and Silicone GE7207, GE7158, SF1202, SF1173, SF-96 and SF-1066 (all available from General Electric Co [USA]).

Non-volatile silicone oils which are suitable for incorporation in compositions herein can comprise polyalkylsiloxanes, polyalkarylsiloxanes or polyether siloxane copolymers, typically having a viscosity of above 10 mPa.s at 25° C. Many non-volatile silicone oils have a viscosity often up to about 2000 mPa.s, and others have a still higher viscosity, such as up to about $10^6$ to $5 \times 10^6$ mPa.s. Examples of suitable non-volatile polyalkylsiloxanes are available from Dow Corning under the 200 series. Suitable polyalkarylsiloxanes comprise polymethylphenylsiloxanes having a viscosity of from about 15 to 65 censtistoke at 25° C., such as those available from Dow Corning as 556 fluid. Suitable polyether siloxanes comprise dimethylpolyoxyalkalene ether copolymers (dimethicone copolymers) which often have a viscosity of from 1200 to 1500 censtistoke at 25° C., such as a polysiloxane ethylene glycol ether copolymer. Yet other suitable non-volatile silicone oils comprise or contain dimethicone/alcohol polymers (dimethiconols).

The oil phase can comprise, if desired a liquid hydrocarbon, such as a mineral oil, paraffin oils, petrolatum or hydrocarbon oils. The hydrocarbon can provide the balance of the oil phase, together with or instead of the aforementioned silicone oils. The proportion of liquid hydrocarbon in the emulsion is commonly selected in the range of from 0 to 15% w/w and particularly 0 to 5% w/w. The oil phase can additionally include a waxy hydrocarbon, such as paraffin waxes, hydrogenated castor oil, Synchrowax HRC, Carnabau, beeswax, modified beeswaxes, microcrystalline waxes, and polyethylene waxes.

The oil phase can alternatively or preferably additionally comprise a water-insoluble aliphatic alcohol. Such alcohols often contain from at least 8, and particularly from 10 30 carbons, and may be linear or branched. Examples include myristyl alcohol octyldodecanol or isocetyl alcohol. The insoluble alcohol often constitutes from 0 to 5% w/w, and in some embodiments from 0.1 to 1% w/w of the emulsion.

The oil phase can desirably include emollient aliphatic esters often containing from about 12 to 25 carbons which contain a long chain (usually containing at least 12 carbons) and short chain alkyl group (usually containing from 2 to 6 carbons), derivable from an acid and alcohol, or vice versa. Examples of such ester include cetyl octanoate, cetyl lactate, myristyl lactate, cetyl palmitate, butyl myristate, butyl stearate, decyl oleate, cholesterol isostearate, myristyl myristate, glyceryl laurate, glyceryl ricinoleate, glyceryl stearate, alkyl lactate, alkyl citrate, alkyl tartrate, glyceryl isostearate, hexyl laurate, isobutyl palmitate, isocetyl stearate, isopropyl isostearate, isopropyl laurate, isopropyl linoleate, isopropyl myristate, isopropyl palmitate, isopropyl stearate, isopropyl adipate, propylene glycol monolaurate, propylene glycol ricinoleate, propylene glycol stearate, and propylene glycol isostearate. Many of the foregoing esters can also contribute to emulsification of the formulation, and partiuclarly as a co-emulsifier with a comparatively low HLB value. Other suitable esters comprise plasticiser esters, ie short chain alkyl esters of aryl di or tri carboxylic acids, such as diethyl or dibutyl phthalate. The esters are often incorporated in the emulsion in the proprtion of from 0 to 10% w/w and in many formulations from 0.5 to 5% w/w.

The oil phase can also comprise an aliphatic ether such as in particular an ether derived from a polyalkylene glycol and an aliphatic alcohol, such as especially a C2 to C6 aliphatic alcohol, and particularly butyl alcohol. The polyalkylene glycol often contains from 10 to 20 units and is preferably a polypropylene glycol. A particularly suitable example comprises polypropylene glycol 13 butyl ether. The proportion of ether in the emulsion is often selected in the range of from 0 to 10% w/w and particularly from 1 to 5% w/w.

It will be understood that the oil phase in the emulsion often contains a mixture of constituents, such as a silicone oil such as particularly a volatile silicone oil, and/or a hydrocarbon together with at least one of a polypropylene ether, an aliphatic ester and an aliphatic alcohol.

The oil phase often incorporates a fragrance oil, in many instances selected in the range of from 0 to 5% w/w, especially from 0.1 to 2% w/w and in many instances from 0.5 to 1% w/w.

Emulsifier

The emulsion incorporates one or more emulsifiers, which often are non-ionic. The proportion of emulsifier in the emulsion is often selected in the range of from 1.5 to 10% w/w, and in many instance from 2 to 5% w/w. It is convenient to select at least one emulsifier which has an HLB value of at least 8 and often at least 10, eg 10 to 18. It is further convenient to select one or more co-emulsifiers which has an HLB value of bellow 8 and particularly from 2 to 6. By employing the two emulsifiers together in appropriate ratios, it is readily feasible to attain a weighted average HLB value that promotes the formation of an emulsion. For most emulsions according to the present invention, the average HLB value is chosen in the range of about 6 to 12, and for many from 7 to 11 Many suitable emulsifiers are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditols as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil sunflower seed oil or soya bean oil. Such non-ionic surfactants can also be derived from a polyhydroxy compound such as glycerol or sorbitol or other alditols. Examples of emulsifiers include ceteareth-10 to -25, ceteth-10-25, steareth-10-25, and PEG-15-25 stearate or distearate. Other suitable examples include C10–C20 fatty acid mono, di or tri-glycerides. Further examples include C18–C22 fatty alcohol ethers of polyethylene oxides (8 to 12 EO).

The co-emulsifiers, which typically have a low HLB value, and often of from 2 to often comprise mono or possibly fatty acid diesters of polyhydric alcohols such as glycerol, sorbitol, erythritol or trimethylolpropane. The fatty moiety is often from C14 to C22 and is saturated in many instances, including cetyl, stearyl arachidyl and behenyl. Examples include monoglycerides of palmitic or stearic acid, sorbitol mono or diesters of myristic palmitic or stearic acid, and trimethylolpropane monoesters of stearic acid.

Examples of emulsifiers and co-emulsifiers having a suitable HLB value or materials containing such compounds are known to persons skilled in the art and/or can readily be located in reference works such as the Handbook of Cosmetic and personal Care Additives published by Gower and compiled by Ash and Ash. Suitable emulsifiers and co-emulsifiers are widely available under many tradenames including Abil™, Alkamuls™, Arlacel™, Brij™, Chemax™, Cremophor™, Dehydrol™, Emalex™, Emerest™, Empilan™, Emulgade™, Emulin™, Ethylan™, Eumulgin™, Hetoxol™, Lipotin™, Lutrol™, Miranol™, Monomuls™, Myrj™, Pluronic™, Span™, Synperonic™, Tegin™, Tween™, and Volpo™.

Optional ingredients in the invention compositions include disinfectants, for example at a concentration of up to about 6% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™, Triclosan™, Triclorban™ and Chlorhexidine warrant specific mention. A yet another class comprises biguanide salts such as available under the trademark Cosmosil™.

The compositions herein can incorporate one or more cosmetic adjuncts conventionally contemplatable for antiperspirant liquids or creams, for example in amounts of up to about 5% w/w. Such adjuncts includes skin feel improvers, such as talc or finely divided polyethylene, skin benefit agents such as allantoin or lipids, colours, or skin cooling agents other than the already mentioned alcohols, such as menthol and menthol derivatives.

Any deodorants and adjuncts are incorporated or dispersed in the oil or aqueous phase, depending on their solubility characteristics.

Formulations according to the present invention, ie antiperspirant emulsions showing desirable or improved phase stability, even at elevated temperature, such as emulsions obtained by suitably shear mixing a viscous oil in water emulsion containing an hydratable polymer before introduction of the antiperspirant active, have been shown to exhibit highly desirable sensory properties. Formulations containing modified starch have been rated by an experienced panel of testers as providing improved smoothness, sometimes called glide, by comparison, for example, with comparable conventional oil in water antiperspirant emulsions. Moreover, in further tests by the panel, a number of other beneficial attributes were identifiable. In particular, benefits of decreased stickiness of feel and decreased greasiness of feel were reported, particularly during the period shortly following topical application, such as up to around an hour after application. Moreover, compared with the conventional roll-on formulation, a product with reduced visibility of deposit has been observed.

Accordingly, the invention provides roll on formulations having one or more of a smoothness score of at least 50 and preferably at least 55, on application, a stickiness score of at most 18 and preferably at most 15, and a greasy feel score of at most 14 and preferably at most 10 both measured 1 hour after application, when by reference a modified F41-2-6 roll-on formulation containing 20% w/w Al—Zr-glycine antiperspirant active achieved scores of respectively (approximately) 44, 21 and 17.3, the scores being located on a scale of from 0 to 100, 0 indicating none of the attribute at all, whereas 100 indicates the maximum of that attribute. The modified F41-2-6 formulation is a modification of formulation F41-2-6 described in a ICI Speciality Chemicals brochure for "Brij" 721 (trademark of ICI) in which 20% Al—Zr-glycine antiperspirant active replaces 16% aluminium chlorohydrate and 4% balance of water. An alternative way of viewing the data is an improvement on a scale of 0 to 100 of at least 6, preferably at least 11 for smoothness on application, and/or a reduction of at least 3 and preferably at least 6 for stickiness, and/or a reduction of at least 3 and preferably at least 7 for greasy feel, the latter two measured 1 hour after application.

Especially desirably, the invention provides oil in water emulsions which simultaneously have stability, particularly when measured at elevated temperature of 50° C., and one or more of improved smoothness on application, reduced greasy feel and reduced stickiness. Emulsions having such a beneficial combination of properties are obtainable by the process described herein in respect of the first aspect of the present invention employing a hydratable polymer dispersed within an aqueous phase.

The emulsions of the present invention can, if desired, be rendered into creams or gels by introducing a structurant or gellant into the continuous (water) phase. Sufficient structurant or gellant can be introduced to attain the desired increase in viscosity, often selected in the range of from 1 to 6% w/w. The gellant can comprise inorganic thickeners such as silica or clays, eg montmorillonite or hectorite or can comprise polymeric structurants such as polyglycerides including agar, agarose, pectin, guars, and carageenan. Other well known aqueous phase structurants for antiperspirant compositions can alternatively or additionally be employed.

Having described the invention in general terms, specific embodiments will now be described in more detail by way of example only.

Comparisons C1 C3 and C9 and Examples 2, 4 to 8 and 10–16 In these comparisons and Examples, emulsions having the compositions summarised in Table 1 or 2 below were prepared by the following method—200 g scale.

Step 0 —An aqueous phase was prepared by mixing water and glycerol and heating it to 80° C. An oil phase was prepared by mixing its ingredients including the emulsifier(s) and heating it to 80° C.

Step i)—The aqueous phase was poured into the oil phase and homogenised using a Silverson homogeniser forming an opaque fluid. The starch powder (if any) was then added to the opaque fluid and the mixture heated in an oil bath at 80° C. and mixed at a fixed speed of 4500 rpm in the homogeniser Step ii)—The mixture continued to be mixed at the same rate and temperature for 20 min in the Silverson homogeniser, during which period the starch polymer became hydrated and the emulsion became visibly more viscous.

Step iii)3: The emulsion was cooled down to 30° C. while continuing to be mixed with a homogeniser at 4500 rpm.

Step iv): The antiperspirant active solution and perfume (each at laboratory ambient) were added to the emulsion and mixed with an over-head mixer (homogeniser) at 4500 rpm.

TABLE 1

| | Comparison/Examples | | | | | | | |
|---|---|---|---|---|---|---|---|---|
| ingredients | C1 % w/w | 2 % w/w | C3 % w/w | 4 % w/w | 5 % w/w | 6 % w/w | 7 % w/w | 8 % w/w |
| oil phase | | | | | | | | |
| Hydrocarbon wax | 0.65 | 0.65 | 0.65 | 0.65 | 1.3 | 1.3 | 1.3 | 0.65 |
| glycerol monostearate | 0.5 | 0.5 | 0.5 | 0.5 | 1.0 | 1.0 | 1.0 | 0.5 |
| co-emulsifier - Emulgin B2 | 0.4 | 0.4 | 0.4 | 0.4 | 0.4 | 0.6 | 0.8 | 0.4 |
| Emulsifier Emulgade SE | 2.0 | 2.0 | 2.0 | 2.0 | 2.0 | 3.0 | 4.0 | 2.0 |
| Cyclomethicone (penta) | 5.0 | 5.0 | 5.0 | 5.0 | 3.5 | 3.5 | 3.5 | 3.5 |
| Octyldodecanol | 0.5 | 0.5 | 0.5 | 0.5 | 0.5 | 0.5 | 0.5 | 0.5 |
| Hydrogenated castor wax | — | — | — | — | 1.0 | 1.0 | 1.0 | — |
| PPG-13 butyl ether | — | — | — | — | 3.5 | 3.5 | 3.5 | 3.5 |
| PEG-8 Distearate | — | — | — | — | — | — | — | 1.0 |
| water phase | | | | | | | | |
| Water | 36.45 | 35.45 | 35.4 | 35.45 | 45.8 | 44.6 | 43.4 | 48.95 |
| Glycerol starch | 4.0 | 4.0 | 4.0 | 4.0 | 2.0 | 2.0 | 2.0 | 2.0 |
| cationic potato starch | — | — | — | 1.0 | | | | |

TABLE 1-continued

| ingredients | Comparison/Examples | | | | | | | |
|---|---|---|---|---|---|---|---|---|
| | C1 % w/w | 2 % w/w | C3 % w/w | 4 % w/w | 5 % w/w | 6 % w/w | 7 % w/w | 8 % w/w |
| Amylofax HB Unmodified potato starch | — | — | 1.0 | — | | | | |
| Amphoteric potato starch Solanace later additions | — | 1.0 | — | — | 1.0 | 1.0 | 1.0 | 1.0 |
| Al—Zr pentachloro-hydrate (40%) | 50 | 50 | 50 | 50 | — | — | — | — |
| Al chloro-hydrate (50%) | — | — | — | — | 35 | 35 | 35 | 35 |
| Perfume | 0.5 | 0.5 | 0.5 | 0.5 | 1.0 | 1.0 | 1 | 1.0 |
| Properties | | | | | | | | |
| Stable at 50° C. | No | Yes | No | Yes | Yes | Yes | Yes | Yes |
| Stable at 0–45° C. cycling | No | Yes | nd | nd | nd | nd | nd | nd |
| SWR % | nd | 36 | nd | nd | nd | nd | nd | nd |

From Table 1, it can be seen that the emulsions that was produced without modified starch was unstable to storage at a moderately elevated temperature such as could be encountered during storage in the tropics or in summer conditions in warehouses in many sub-tropical countries of the world. On the other hand, the similar emulsions that were produced containing the modified starches dispersed through the emulsion demonstrated stability.

Table 1 also shows that under the conditions prevailing, the dispersion of unmodified starch was unable to generate a stable emulsion. Data shown in Table 3 hereinafter shows that the unmodified starch was unable to increase the viscosity of the emulsion to a level at which shear mixing was able to reduce the droplet size of the oil phase.

Further Examples and a comparison include the following summarised in Table 2 below.

TABLE 2

| ingredients | Comparison/Examples | | | | | | | |
|---|---|---|---|---|---|---|---|---|
| | C9 % w/w | 10 % w/w | 11 % w/w | 12 % w/w | 13 % w/w | 14 % w/w | 15 % w/w | 16 % w/w |
| oil phase | | | | | | | | |
| Steareth-21 | 1.7 | 1.7 | 1.25 | 1.7 | 1.7 | 2.0 | 1.5 | 1.5 |
| Steareth-2 | 1.7 | 1.7 | 0.75 | 1.7 | 1.7 | 0.5 | 0.5 | 0.5 |
| Cetearyl alcohol | — | — | 0.5 | — | | | | |
| Cyclomethicone (tetra) | — | — | 5.0 | 5.0 | 5.0 | 3.0 | 3.0 | 3.0 |
| Octadodecanol | — | — | 0.5 | 0.5 | 0.5 | 0.5 | 0.5 | 0.5 |
| Fluid AP | — | — | 2.0 | — | | | | |
| PPG-15 stearyl ether | 3.3 | 3.3 | | 3.3 | | | | |
| Emulsifying wax | | | | | 0.65 | | | 0.5 |
| Glyceryl stearate | | | | 0.5 | 0.5 | 0.5 | 0.5 | |
| aqueous phase | | | | | | | | |
| Water | 42.8 | 41.8 | 51.0 | 36.6 | 34.45 | 40.0 | 40.5 | 40.0 |

TABLE 2-continued

| ingredients | Comparison/Examples | | | | | | | |
|---|---|---|---|---|---|---|---|---|
| | C9 % w/w | 10 % w/w | 11 % w/w | 12 % w/w | 13 % w/w | 14 % w/w | 15 % w/w | 16 % w/w |
| Glycerol | — | — | 2.0 | 4.0 | 4.0 | 2.0 | 2.0 | 2.0 |
| Starch | | | | | | | | |
| Amphoteric Starch Solanace later additions | — | 1.0 | 1.0 | 1.0 | 1.0 | 1.0 | 1.0 | 1.0 |
| Al—Zr tetrachloro-hydrate (35%) | | | | | | | | |
| Al—Zr pentachloro-hydrate (40%) | 50.0 | 50.0 | — | 50.0 | 50.0 | 50.0 | 50.0 | 50.0 |
| Al chloro-hydrate (50%) | — | — | 35.0 | — | | | | |
| Perfume | 0.5 | 0.5 | 1.0 | 0.5 | 0.5 | 0.5 | 0.5 | 0.5 |
| Properties | | | | | | | | |
| Stable at 50° C. | No | Yes | Yes | Yes | | | | |
| Stable at 0–45° C. cycling | No | Yes | nd | nd | | | | |

Measurement of Properties
Stability

Where it was measured, the stability of the formulations was tested by transferring a sample (approximately 100 g) into a clear glass powder jar and storing it in a room maintained at 50° C. or subject to alternation at 12 hourly intervals at either 0° C. or 45° C. The emulsions were observed after 14 days storage for changes in their appearance and in particular for signs of cracking (breaks in the emulsion shape), creaming (oil layer formation) or phase separation (changes in opaqueness at various heights of the emulsion.)

Particle Size Analysis

Light microscopy was used as a qualitative test to assess the droplet size distributions. An OLYMPUS BH-2 light microscope was calibrated using a graticule for the various objective lens. A minimum of 300 droplets were assessed and the maximum and minimum droplet sizes were noted.

Quantitative information on the droplet size and distribution was obtained using a laser light scattering technique.

Diluted samples were placed in a Malvern MasterSizer X (Malvern Instruments Ltd., UK, model MSX04LA). A 45 mm Range Lens (0.1–80 mmange) was connected to a sampling unit (MS23 Cell) and the data was analysed using the Mastersizer software version 1.2a which produced a mean volume weighted particle diameter.

Viscosity and Shear Stress Measurements

These were measured at laboratory ambient (23° C.), unless otherwise stated.

A Brookfield DV-1+viscometer was used to measure the emulsion viscosities. An RV spindle #3 was used at spindle speeds of 10 rpm and 20 rpm.

A Carri-Med rheometer and a Haake rheometer were used to obtain flow curve data (Viscosity versus shear stress profiles) for some of the emulsions. Full flow curves, from low stress to high shear rate, were produced by combining data from the foregoing controlled stress and controlled shear rate instruments. Measurements were carried out on a Carri-Med controlled stress rheometer (using a vane and basket measuring system) from a stress of 1 Pa up to the stress required to provide a shear rate of 1 (1/s). Measurements from shear rates of 0.3(1/s) to 300 (1/s) were made using a Haake RV20 viscometer (with an SV2P measuring head). The data from the two instruments was then combined to give the complete flow curve on which the Shear Stress is determined.

Starch Structure Characterisation

The starch containing emulsions were diluted with 2-fold distilled water. The diluted sample was dyed by the same volume of 0.01N Iodine/distilled water solution. The samples were assessed by light microscopy with the starch showing up as dark blue against the background.

The viscosity (Brookfield at 10 rpm) and mean droplet size of Comparisons 1 and 3 and Examples 2 and 4 are summarised below in Table 3.

TABLE 3

|  | Comparison/Examples | | | |
| --- | --- | --- | --- | --- |
|  | C1 | C3 | 2 | 4 |
| viscosity (mpa · s) | 200 | 90 | 11000 | 18300 |
| Mean droplet size ($\mu$m) | 1.4 | 1.2 | 0.6 | 0.4 |
| Newtonian plateau viscosity (mPa · s) | nm | 22 | 1000 | 300 |
| Critical Stress (Pa) | nm | 1.1 | 47.6 | 20 |

From Table 3, and by comparing C1 with Examples 2 and 4, it can be seen that the invention products enjoyed a considerably higher viscosity than the corresponding product without incorporation of the amphoteric or cationic starch and a significantly lower mean droplet size. If Comparison C3 is compared with comparison 1, it can also be seen that incorporation of unmodified starch under the same conditions neither increased the viscosity of the emulsion nor reduced the mean droplet size of the emulsion to any like the same extent as when employing the modified starch. By comparison with the data summarised in Table 1, it is apparent that there is a correlation between the stability of the emulsions described in Table 1 and the physical measurements summarised in Table 3.

Analysis of the graph of populations of droplets against their size shows for Comparison 1 that it had a double peak, centring at about 0.4 and 2.5 $\mu$m, whereas the emulsion of Example 2 showed a single peak, centred at about 0.6 $\mu$m, with approximately 75% of the droplets within the range of ½ to 2×the mean droplet size.

Emulsion 2 also included some very large particles (peaking at around 30 $\mu$m) attributable to swollen starch domains.

Stability Measurement

In this Example, the stability of the formulation according to Example 13 was measured by observing changes in the mean droplet size of the oil phase in the emulsion.

The mean droplet size of Example 13 formulation was compared with the same formulation employed for comparison against the Example 17 formulation.

An emulsion sample was stored in an oven equilibrated at 50° C. After 24 hours the emulsion was sampled with a pipette. The samples were taken in the middle of the container and this was done by simply measuring the height of the emulsion in the container and taking samples at half its height. Several samples were taken and the mean droplet size was recorded (measured using the Malvern). The measurements were repeated periodically in the same manner.

Measurements on the Example 14 formulation showed that over a period of 13 days the half-height mean droplet size stayed constant and below 1 $\mu$m, (approximately 0.8 $\mu$m, within the normal variations of experimental determinations using that apparatus. The constant droplet size of Example 14 formulation shows that it is resistant towards creaming. By contrast, the measurements on the comparison emulsion not produced by a process of the present invention showed an initial mean droplet size of approximately 3.5 mm that had fallen after only 24 hours to 0.6 mm, though the mean droplet size remained similar for the remainder of the storage time of 13 days. The initial drop in droplet size demonstrates creaming behaviour of the emulsion which was not reversed on storage.

EXAMPLE 17

Sensory Properties

Sensory properties are evaluated by a panel of evaluators. Evaluators undergo extensive training to ensure the consistency and sensitivity of their sensory assessments, involving assessing a range of standard systems that exemplify various levels for each key sensory attribute.

Product Application

Products are applied by evaluators in a measured dose of 300 mg +/− 30 mg for roll-ons of coded formulations.

Protocol

Evaluators remove underarm hair 24 hours prior to testing. All testing is carried out in a controlled testing area, employing at least 14 evaluators. Evaluators are instructed to wash both their underarms and forearms with unperfumed Lux™ soap in luke warm water and to dry thoroughly before applying test products.

Evaluators apply the first product to their left underarm and complete the relevant score sheet. The strength and intensity of each product's sensory attributes are recorded on a descriptively anchored and divided 10 cm line scale. When the left underarm score sheet is completed, a second product is applied to the right underarm and the process is repeated on a second score sheet. The evaluators' marks on the line scales are converted into scores on a 1–100 scale. Mean scores are then calculated for each sensory attribute for each product. Evaluators leave the products on their underarms unless any discomfort is reported.

In Example 17, an invention formulation summarised in Table 4 and produced by the same process as for Example 2 was compared for its sensory properties against a conventional oil in water roll-on formulation produced in a conventional process and containing the same concentration of the same AL—Zr-glycine antiperspirant active, but no starch, based on Formulation F41-2-6 Roll-on antiperspirant, containing Arlamol E, Brij 72 and Brij 721 emulsifiers.

TABLE 4

| Ingredient | % w/w |
| --- | --- |
| Al—Zr glycine soln (40% | 50.00 |
| Perfume | 0.50 |
| Water | 37.6 |
| Wax | 0.5 |
| Glyceryl monostearate | 0.5 |
| Emulgade SE emulsifier | 2.0 |
| Eumulgin B2 co-emulsifier | 0.4 |
| Octyl dodecanol | 0.5 |
| Cyclomethicone | 5.0 |
| Glycerol | 2.0 |
| Starch | 1.0 |

TABLE 5

| Attribute | Score Ex 13 | Conventional Roll-on |
|---|---|---|
| Sticky feel (1 hr) | 11.91 | 21.08 |
| Greasy feel (1 hr) | 7.45 | 17.33 |
| Glide (Smoothness) | 61.75 | 43.83 |

From Table 5, it can be seen that the evaluators' mean score for the invention product was substantially higher for glide than that for the conventional roll-on. Likewise, the evaluators' scores for sticky feel and greasy feel were markedly lower for the invention composition compared with that for the conventional roll-on after 1 hour, ie in a period soon after application of the antiperspirant which is particularly important for users of antiperspirant, since it is the period in which their initial or early impressions are formed.

What is claimed is:

1. A process for producing an antiperspirant-containing emulsion comprising the steps of:
    i) dispersing a hydratable polymer in an aqueous emulsion comprising an aqueous phase, an oil phase and an emulsifier at a concentration and at a temperature selected such that the polymer is hydrated and the viscosity of the emulsion is substantially higher than in the absence of the polymer,
    ii) subjecting the emulsion containing the dispersion of hydratable polymer to high shear,
    iii) agitating the emulsion until its temperature has attained a temperature below 40° C. and
    iv) introducing an antiperspirant salt into the emulsion with agitation to form an antiperspirant emulsion.

2. A process according to claim 1 wherein the emulsion that is subjected to high shear in step ii) has a Newtonian plateau viscosity at a shear stress of 10 Pa of from 50 to 20 000 mPa.s.

3. A process according to claim 1 wherein the emulsion that is subjected to high shear in step ii) has a Critical Stress of from 5 to 2000 Pa.

4. A process according to claim 1 wherein the hydratable polymer comprises an amphoteric or cationic starch.

5. A process according to claim 1 wherein in step i) the hydratable polymer is dispersed at a temperature selected in the range of from 60 to 100° C.

6. A process according to claim 1 wherein the emulsion in step i) is obtained by forming separately aqueous and oil compositions, heating them to the elevated temperature and mixing to form the emulsion.

7. A process according to claim 1 wherein the emulsion containing the hydratable polymer in step i) has a viscosity in the range of from 10000–20000 mPa.s.

8. A process according to claim 1 wherein the emulsion in step i) comprises from 25 to 75 parts by weight aqueous phase, 2 to 20 parts by weight oil phase and 1 to 7.5 parts by weight emulsifier.

9. A process according to claim 1 wherein in step i), the weight ratio of hydratable polymer to oil phase is in the range of from 1:2 to 1:20.

10. A process according to claim 1 wherein the antiperspirant emulsion is obtained in step iv) by mixing an aqueous solution of antiperspirant salt with the emulsion of step iii).

11. A process according to claim 1 wherein the mixture of hydratable polymer and emulsion is subjected to a shear rate of greater than 2000 rpm, and particularly 3000 to 5000 rpm.

12. A process according to claim 1 wherein the antiperspirant emulsion obtained in step iv) contains from 10 to 50% and preferably 15 to 30% by weight antiperspirant salt.

13. A process according to claim 1 wherein the antiperspirant salt introduced in step iv) comprises an aluminium chlorohydrate, or a zirconium aluminium chlorohydrate or complex of either.

14. A process according to claim 1 wherein the antiperspirant salt is a zirconium-containing antiperspirant active.

15. A process according to claim 1 wherein the antiperspirant emulsion comprises from 1.5 to 10% w/w emulsifier, from 70 to 95% w/w aqueous phase including from 0.25 to 5% w/w hydratable polymer and from 1 to 25% w/w dispersed oil phase, having a mean particle size of below 1 µm.

16. A process according to claim 12 characterised in that the antiperspirant emulsion obtained in step iv) has a viscosity of less than 10000 mPa.s.

17. A process according to claim 1 comprising
    i) dispersing a hydratable polymer in an aqueous mixture emulsion comprising an aqueous phase, an oil phase and an emulsifier at an elevated temperature of above 60° C. to form a viscous emulsion,
    ii) subjecting the emulsion containing the dispersed hydratable polymer in the to high shear at elevated temperature until one of the phases is dispersed and has a mean droplet size of below 1 µm,
    iii) agitating the dispersion until its temperature has fallen to below 40° C. and
    iv) introducing an antiperspirant salt into the emulsion with agitation to form an antiperspirant emulsion.

18. An antiperspirant emulsion which comprises an aqueous phase containing an antiperspirant salt, a dispersed oil phase and an emulsifier characterised in that the aqueous phase contains from 0.25 to 5% w/w hydratable polymer and at least 10% w/w antiperspirant salt and the dispersed oil phase has a mean droplet size of below 1 µm.

19. An antiperspirant emulsion according to claim 18 wherein comprises 1.5 to 10% w/w emulsifier, 70 to 95% w/w aqueous phase, and from 1 to 25% w/w dispersed oil phase.

20. An antiperspirant emulsion according to claim 18 wherein the hydratable polymer comprises an amphoteric or cationic starch.

21. An antiperspirant emulsion according to claim 18 wherein it has a viscosity of from 500 to 5000 mPa.s.

22. An antiperspirant emulsion according to claim 18 wherein the aqueous phase contains from 10 to 50 and w/w antiperspirant salt.

23. An antiperspirant emulsion according to claim 18 wherein the dispersed oil phase has a mean droplet size of from 0.3 to 0.8 µm.

24. An antiperspirant emulsion according to claim 18 wherein the oil phase includes from 3 to 10% w/w of a volatile silicone and/or a volatile hydrocarbon.

25. An antiperspirant emulsion according to claim 18 wherein the aqueous phase contains from 1 to 8%, humectant.

26. An antiperspirant emulsion according to claim 25 wherein the humectant is glycerol.

27. An antiperspirant emulsion according to claim 18 wherein the antiperspirant salt introduced in step iv) comprises an aluminium chlorohydrate, or a zirconium aluminium chlorohydrate or complex of either.

28. An antiperspirant emulsion according to claim 27 wherein the antiperspirant salt is a zirconium aluminium chlorohydrate or complex thereof.

29. An antiperspirant emulsion according claim 18 wherein it is stable for at least 2 weeks storage at a temperature of 50°.

30. An antiperspirant emulsion according to claim 18 wherein it contains additionally a structurant in an amount sufficient to gel or solidify the emulsion.

31. An antiperspirant composition comprising an aqueous emulsion having a dispersed oil phase wherein the aqueous phase contains an effective concentration of an antiperspirant salt which is stable to phase separation in a stability test at 50° C.

32. An emulsion according to claim 31 wherein the content of antiperspirant salt is at least 10% w/w of the aqueous phase.

33. An emulsion according to claim 31 wherein the antiperspirant salt contains zirconium and aluminium and is preferably a zirconium aluminium complex.

34. An emulsion according to claim 31 wherein the emulsion has a viscosity of less than 10000 mPa.s and preferably from 500 to 5000 mPa.s.

35. An emulsion according to claim 31 wherein the emulsion has at least one of a smoothness score of at least 50, a greasy feel score of at most 14 and a stickiness score of at most 18 1 hour after application.

36. An emulsion which comprises an aqueous phase containing a salt, a dispersed oil phase and an emulsifier wherein the aqueous phase contains from 0.25 to 5% w/w of a dispersed hydratable polymer and at least 10% w/w dissolved salt and the dispersed oil phase has a mean droplet size of below 1 μm.

37. An emulsion according to claim 36 wherein the aqueous phase is acidic.

38. An emulsion according to claim 36 wherein it comprises 1.5 to 10% w/w emulsifier, from 70 to 95% w/w aqueous phase and from 1 to 25% w/w dispersed oil phase.

39. An emulsion according to claim 36 wherein it has a viscosity of less than 10000 mPa.s.

40. A process according to claim 3, wherein the emulsion is subjected to high shear in step ii) has a Critical Stress of from 10 to 500 Pa.

41. A process according to claim 8, wherein the weight ratio of water to oil phases is in the range of 2.5:1 to 30:1.

42. A process according to claim 9, wherein the weight ratio of hydratable polymer to oil phase is in the range of from 1:2.5 to 1:12.

43. A process according to claim 12, wherein the antiperspirant emulsion obtained in step ii) contains from 15 to 30% by weight antiperspirant salt.

44. A process according to claim 16, wherein the antiperspirant emulsion obtained in step iv) has a viscosity preferably from 500 to 5000 mPa.s.

45. An antiperspirant emulsion according to claim 21 which has the viscosity of from 1000 to 2000 mPa.s.

46. An antiperspirant emulsion according to claim 22 wherein aqueous phase contains of from 15 to 30% w/w antiperspirant salt.

47. An antiperspirant emulsion according to claim 25, wherein the aqueous phase contains from 1.5 to 5% humectant.

48. An emulsion according to claim 33, wherein the antiperspirant salt is a zirconium aluminium complex.

49. An emulsion according to claim 39, wherein the viscosity of said emulsion is preferably from 500 to 5000 mPa.s.

50. A method for controlling perspiration which comprises topically applying a composition according to claim 18 to human skin.

* * * * *